United States Patent [19]

Mack

[11] 4,431,413
[45] Feb. 14, 1984

[54] COMBINATION APPLIANCE FOR HOLDING AND FIXING A TRANSFER BOW

[76] Inventor: Heinz Mack, Südl. Auffahrtsallee 64, 8000 München 19, Fed. Rep. of Germany

[21] Appl. No.: 331,991

[22] Filed: Dec. 17, 1981

[30] Foreign Application Priority Data

Dec. 24, 1980 [DE] Fed. Rep. of Germany ....... 3049057

[51] Int. Cl.$^3$ ............................................. A61C 19/04
[52] U.S. Cl. ......................................... 433/73; 433/56
[58] Field of Search ............................. 433/73, 54, 56

[56] References Cited

U.S. PATENT DOCUMENTS 3,218,716 11/1965 Stuart .................................... 433/73
3,552,020 1/1971 Weber ................................... 433/73

Primary Examiner—Robert Peshock
Attorney, Agent, or Firm—Larson & Taylor

[57] ABSTRACT

The present invention relates to a combination appliance, also known as a mounting aid, for holding and fixing a transfer bow, for pivotably holding and setting the desired angle of inclination of a frame part of an articulator, and for fixing superimposed jaw casts while mounting the cast of the opposite jaw in the articulator, by means of plaster of Paris. For this purpose, the combination appliance possesses a U-shaped cradle, the base surface of this cradle forming the setting-up surface, in order to guarantee that the combination appliance stands securely. A support for the transfer bow is fitted near the upper end of each sidewall, this support forming several supporting points, it being possible to fix the transfer bow on the support by means of a locking device. In addition, a movable pintle for the frame part of the dental articulator is located near the support, this pintle pointing into the interior space between the sidewalls, and being made in such a way that it is possible to set the dental articulator to the particular angle of inclination desired. Furthermore, a support column and a carrier block, which is height-adjustable and carries a resilient extension arm, are located on one of the sidewalls of the combination appliance, or on a portion of the support rail, which may be extended, this column and block being provided for the purpose of fixing superimposed jaw casts while the cast of the opposite jaw is mounted in the articulator by means of plaster of Paris.

9 Claims, 4 Drawing Figures

COMBINATION APPLIANCE FOR HOLDING AND FIXING A TRANSFER BOW

DESCRIPTION

The present invention relates to a combination appliance, also known as a mounting aid, for holding and fixing a transfer bow, for pivotably holding and setting the desired angle of inclination of a frame part of an articulator, and for fixing superimposed jaw casts while mounting the cast of the opposite jaw in the articulator by means of plaster of Paris.

Jaw casts are transferred into the dental articulator by means of a transfer bow, which employs three reference points on the skull to set the reference plane in relation to the occlusion plane of the teeth, thus enabling the jaw casts to be transferred into the articulator, and mounted in the same positions with respect to the reference plane.

For attaching the anatomical transfer bow, needed for this purpose, to the articulator, only a baseplate, equipped with a vertical rod (stand) carrying a clamp-type holding device, was previously in general use for holding the jaw casts, this arrangement inevitably entailing mechanical problems resulting from twisting and maladjustment.

It is accordingly an object of the present invention to provide an appliance for holding and fixing an anatomical transfer bow, in which the support for this bow is designed in such a way that mechanical problems due to twisting no longer occur, and the arms of the transfer bow are prevented from splaying-out in a scissors-like manner. Expressed in other words, an object of the present invention was to clamp the transfer bow directly onto the frame part of the articulator and, in particular, in such a way that the upper part of the frame of the dental articulator cannot slip down.

Furthermore, it is an object of the present invention to configure the combination appliance in such a way that it is suitable for receiving the frame part of the articulator itself, in order to be able to vary the angular inclination of the occlusion plane, thereby enabling the centering register to be brought into superposition with the cast of the lower jaw, without any tendency to tilt, and enabling mounting to be carried out reliably and quickly, without manual assistance.

An additional object of the present invention is to provide the combination appliance with a device which allows the superimposed jaw casts to be fixed, while mounting the cast of the opposite jaw in the articulator, by means of plaster of Paris.

The purpose of the present invention is consequently to produce a combination appliance which is suitable both for holding and fixing a transfer bow, and for holding and adjusting the desired angle of inclination of a frame part of an articulator, and for fixing superimposed jaw casts while mounting the cast of the opposite jaw in the articulator, by means of plaster of Paris.

With regard to the holding and fixing of a transfer bow, the object is achieved by means of (a) a cradle, of U-shaped cross-section, the sidewalls, of this cradle, which are preferably arranged perpendicularly to the base surface, being located so that they converge towards one another, with, on the one hand the angle of approach corresponding to the angle between the outer edges of the side arms of the transfer bow, which is attached to the upper frame part of the dental articulator, and, on the other hand, the distance between the sidewalls, on the tapering side, being small enough to allow articulator frame parts to be hung therein, (b) supports being located near the upper ends of the vertical sidewalls, and locking devices, known per se, preferably locking screws, being located on the portions, which may be bent over, of the upper ends of the vertical sidewalls for the purpose of holding and fixing a transfer bow.

The object of producing an appliance for pivotably holding and setting the desired angle of inclination of a frame part of an articulator is achieved by means of a design wherein two pintles are located on the inner sides of the vertical sidewalls, near those points on the upper ends which come closest to each other as a result of the approach angle, these pintles being located at right angles to the sidewalls, and at least one of the pintles being capable of movement in its longitudinal axis, while both of them can project into recesses situated in the frame part of the articulator.

The object of producing a device for fixing superimposed jaw casts while the cast of the opposite jaw is being mounted in the articulator, by means of plaster of Paris, is achieved by a design wherein a support column, equipped with a carrier block, which carries a resilient extension arm and is height-adjustable, is located on one of the sidewalls of the combination appliance, or on a portion of the support rail, which may be extended.

The subject of the invention is consequently a combination appliance for holding and fixing a transfer bow, for pivotably holding and adjusting the desired angle of inclination of a frame part of an articulator, and for fixing superimposed jaw casts while mounting the cast of the opposite jaw in the articulator, by means of plaster of Paris.

(a) a cradle, of U-shaped cross-section is used, the sidewalls of this cradle, which are preferably arranged perpendicularly to the base surface, being located so that they converge towards one another, with, on the one hand, the angle of approach corresponding to the angle between the outer edges of the side arms of the transfer bow, which is attached to the upper frame part of the dental articulator, and, on the other hand, the distance between the sidewalls, on the tapering side, being small enough to allow articulator frame parts to be hung therein, (b) supports are located near the upper ends of the vertical sidewalls, and locking devices known per se, preferably locking screws, are located on the portions, which may be bent over, of the upper ends of the vertical sidewalls, for the purpose of holding and fixing a transfer bow.

(c) for pivotably holding and setting the desired angle of inclination of a frame part of an articulator, two pintles are located on the inner sides of the vertical sidewalls, near those points on the upper ends which come closest to each other as a result of the approach angle, these pintles being located at right angles to the sidewalls, and at least one of the pintles being capable of movement in its longitudinal axis, while both of them can project into recesses situated in the frame part of the articulator, and (d) for fixing superimposed jaw casts while the cast of the opposite jaw is being mounted in the articulator, by means of plaster of Paris, a support column, equipped with a carrier block, which carries a resilient extension arm and is height-adjustable, is located on one of the sidewalls, or on a portion of the support rail, which may be extended.

In accordance with the invention, an appliance is consequently produced, which enables the anatomical transfer bow to be set down in a stable manner and to be securely fixed, with the upper part of the articulator suspended therein, while the cast of the upper jaw is mounted, it being possible, after supporting the bite fork, to swing the upper part of the articulator completely open, and to close it again after applying the plaster of Paris to the mounting plate.

In addition, an appliance for mounting the cast of the lower jaw is provided, according to the invention. For this purpose, the articulator can be suspended the other way round, with the lateral viewing holes of the condylar elements between the spring-mounted, inward-pointing pins of the mounting aid. By altering the support of the cutting pin, which is shortened by 10 mm beyond the calibration, it becomes possible to rotate the reference plane of the articulator and thereby to align the casts in the vertical direction, these being superimposed by means of the centering register. Mounting errors are precluded by using the plaster of Paris of the correct consistency, corresponding to that of thin cream, and by carefully inserting the balls into the condylar guide elements.

The U-shaped cradle, the base surface of which forms the cradle setting-up surface, ensures that the combination appliance is intrinsically mechanically stable and that it stands securely, since the setting-up surface of the receiving cradle, formed by the base surface, makes it possible for the cradle to rest on an underlying support, in a manner which makes it virtually immovable and secure against tipping. To avoid instabilities relating to the parts for receiving the transfer bow, and/or the dental articulator, the base surface merges integrally into the sidewalls of the cradle. In order to guarantee unobstructed insertion of the anatomical transfer bow, at least one support for the transfer bow is fitted near the upper end of each sidewall, at least one locking device interacting, in each case, with this support, in order to fix the position of the transfer bow following its transfer and insertion into the combination appliance. By this means, the combination appliance according to the invention opens up the possibility of fitting the anatomical transfer bow, with the frame part of the articulator, in such a manner that the latter cannot slip down, since the support, provided according to the invention, on each of the two limb parts distributes the supporting action over several points, so that the anatomical transfer bow, after being set down, rests on the supports in a manner secure against tilting and splaying. After being set down on the supports, the anatomical transfer bow is fixed, in conjunction with the particular locking device assigned to the support, in such a way that the opening angle of the side arms of the transfer bow, which are splayed apart in a scissors shape, reliably remains unchanged, at its original setting.

In addition to the support and the locking device, a movable holding device is also provided in the combination appliance according to the invention, for the frame part of the dental articulator, and for setting the angle of inclination of the latter, this holding device pointing into the interior space between the sidewalls. The combination appliance can, by this means, receive both the anatomical transfer bow and the upper frame part of the dental articulator and, in particular, in a manner which allows the angle of inclination of the occlusion plane to be varied, in order to ensure that the centering-register can be superimposed, together with the cast of the lower jaw, without any tendency to tilt and while simultaneously enabling mounting to be carried out reliably and quickly, without manual assistance.

As a rule, the cast of the lower jaw is placed on the register, as a cast of the opposite jaw, and is pressed against the register and the other jaw half.

The pressure, necessary for this purpose, is produced, according to the invention, by the resilient extension arm which is connected to the support column.

In accordance with the preceding text, the combination appliance according to the invention essentially combines three functions. Firstly, the transfer bow is securely received, supported, held, and fixed, and secondly, the frame part of the articulator is likewise held, offered up, without distortion, to the transfer bow, and the most suitable position for the mounting operation is set, while, thirdly, the jaw casts are locked against each other, under a defined pressure, by means of the resilient extension arm, while they are mounted in the articulator by means of plaster of Paris.

Preferably, the sidewalls of the U-shaped cradle are arranged, symmetrically, at an angle with respect to the central axis of the base surface, in such a way that they enclose an acute angle, corresponding approximately to the angle enclosed between the outer edges of the side arms of the transfer bow. This arrangement ensures that the cradle of the combination appliance is already roughly matched to the external outline of the anatomical transfer bow, so that, as a result of this, guidance is already obtained when inserting the anatomical transfer bow into the combination appliance, this guidance preventing the occurrence of any unintended adjustments, which lead to inaccuracies, resulting directly from knocking the anatomical transfer bow.

Having regard to simplicity of manufacture of the combination appliance, each support is formed by a support rail, which is fastened to the appropriate sidewall. The support rail is expediently a rectangular block, which is fastened, in a simple manner, to the appropriate sidewall, using screw connections. Alternatively, instead of the support rails, it is also possible, according to the invention, to provide appropriately deep grooves, made directly in the sidewalls, which are designed with a corresponding thickness, or to provide two pegs, on each side, which essentially fulfil the same purpose as a support with several supporting points.

Since the support and, in particular, the support rail which is provided in accordance with the invention, presents an adequate supporting surface for the side arms of the transfer bow, it is sufficient to locate, in each case, one locking device at a point approximately in the center of the supporting surface formed by the support. This arrangement favors a constructionally simple embodiment, since only a single locking device is assigned to each support rail.

The locking device is preferably designed as an adjustable locking screw, which bears directly on the side surface of the side arm of an anatomical transfer bow, and presses the latter against the supporting surface formed by the support. That portion of the locking screw which bears on the side surface of the side arm of the transfer bow is preferably designed to be of larger diameter, in order to distribute the locking force over a sufficiently large area, in addition thereby preventing damage to the transfer bow. The portion having this larger diameter is expediently designed in the form of a flat head, and is made of plastic, while the knurled head for turning the locking screw is made of metal.

In order to be able to attach the locking device, particularly the locking screw, to the cradle, in an advantageous manner, the upper end of each sidewall has a portion which is bent over and points inwards, approximately parallel to the base surface of the cradle, this portion being located at such a distance from the support, which is fitted to the inner side of the sidewall, that it is possible to insert the transfer bow, without obstruction, when the locking device is open. However, these bent-over portions also serve at the same time as a means of orientation during the insertion of the transfer bow and, moreover, precisely this portion contains the threaded hole, in which the threaded portion of the locking screw runs. The knurled head of the locking screw projects from this bent-over portion, on its upper surface, so that it is readily accessible and can conveniently be operated in order to fix the transfer bow, without any danger, during this operation, of touching the side arms of the bow.

The holding device, which is movable in its longitudinal axis and is provided for holding the frame part of the dental articulator, can be formed by two movable pintles, which are located near those ends of the sidewalls which are closest to each other.

In order to make it easy to suspend the frame parts of the dental articulator, at least one pintle is mounted so that it can be shifted with respect to its longitudinal axis. To ensure that a pintle of this type, which is mounted in a manner permitting movement, reliably remains in the position in which the articulator is held, the pintle is pre-loaded, by means of a spring, into its position of maximal extension. In order to ensure that the pintle, which can be shifted in its longitudinal axis, has as large range of movement as possible, and also to guide it adequately, the pintle is inserted into a receiving hole in the sidewall and preferably even penetrates the support rail.

The pintle can also form part of the support, in particular, in combination with an additional pintle, located at a distance from the pintle which has the holding function, whereupon both pintles together form the support for the transfer bow. With this arrangement, a multi-point support for the transfer bow is also guaranteed.

A comparatively large base surface of the combination appliance is obtained, according to the invention and while simultaneously ensuring that there is sufficient manipulating space in the region of the supports for the transfer bow and of the holding device for the dental articulator, essentially by arranging that the sidewalls of the cradle, starting from the point at which they merge with the base surface, taper smoothly up to their upper ends. On the other hand, this design also enables material to be saved in forming the cradle, as a result of which the cradle remains relatively light in weight and is thereby easy to handle.

The resilient extension arm, which is preferably made from a thin, resilient plastic rod having a diameter of approximately 3 mm, is located, preferably without being locked, in a hole which is drilled at an angle in the carrier block, which also possesses a vertically drilled hole, through which the support column projects. In order to fix the cast of the opposite jaw, the carrier block is then merely pushed upwards on the support column, and the resilient plastic rod is pushed through the angled hole until its tip just touches the cast of the opposite jaw. The carrier block is then pushed slightly downwards, as a result of which the thin resilient plastic rod bends slightly and at the same time exerts, via its tip, a definite pressure on the cast of the opposite jaw. During this process, the carrier block and the thin resilient plastic rod remain, as a result of tilting, in the positions in which they were set, without any need for additional locking devices. Finally, plaster of Paris is applied to that half of the set of dentures which is located at the top, and the mounting plate of the dental articulator is pressed onto this half. After the plaster of Paris has set, the thin plastic rod is severed, using a pair of scissors, or a side-cutter.

In the text which follows, the invention is explained by reference to FIGS. 1 to 4, which represent, according to the invention, particularly preferred embodiments, but this explanation does not restrict the invention to these embodiments. All details which are not mentioned in the description, but which are evident from the Figures, also belong to the disclosure of the present invention.

Figure 4:
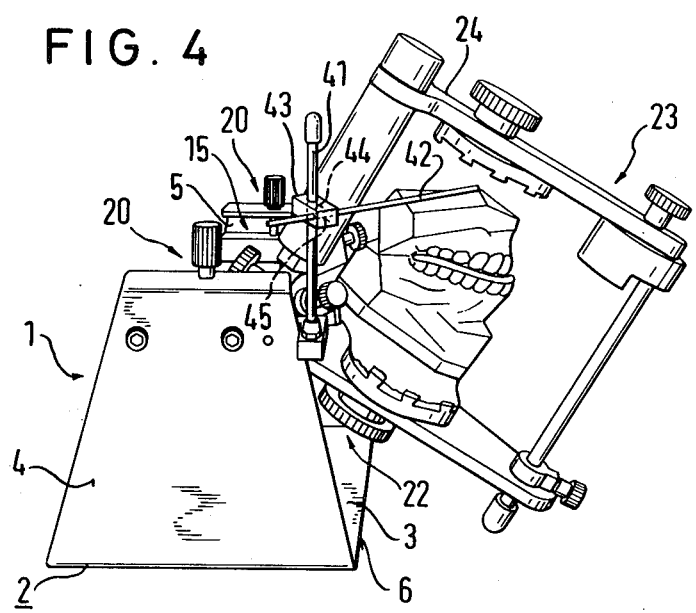

FIG. 4 shows a perspective lateral representation of the combination appliance, with a complete dental articulator, an upper jaw, with centering register, having been mounted in the articulator, by means of plaster of Paris, and a lower jaw having been placed on top, the latter being pressed against the upper jaw, by means of the extension arm, prior to the operation of mounting the lower jaw, by means of plaster of Paris, on the unoccupied, visible mounting plate of the dental articulator.

In FIGS. 1 to 4, the combination appliance is marked 1, in its entirety. In the embodiment represented, the combination appliance 1 is designed as a U-shaped cradle 2. The U-shaped cradle 2 includes a base surface 3 and two sidewalls 4 and 5, which point approximately vertically upwards from the base surface 3. The U-shaped cradle 2, with the base surface 3 and the sidewalls 4 and 5, forms, as a whole, a one-piece component, and is obtained, for example, from one strip of material, by bending appropriately, or is formed by a casting. The base surface serves as a setting-up surface 6 for the combination appliance, this setting-up surface resting on an underlying support 7, such as, for example, a table top or similar surface.

Figure 2:
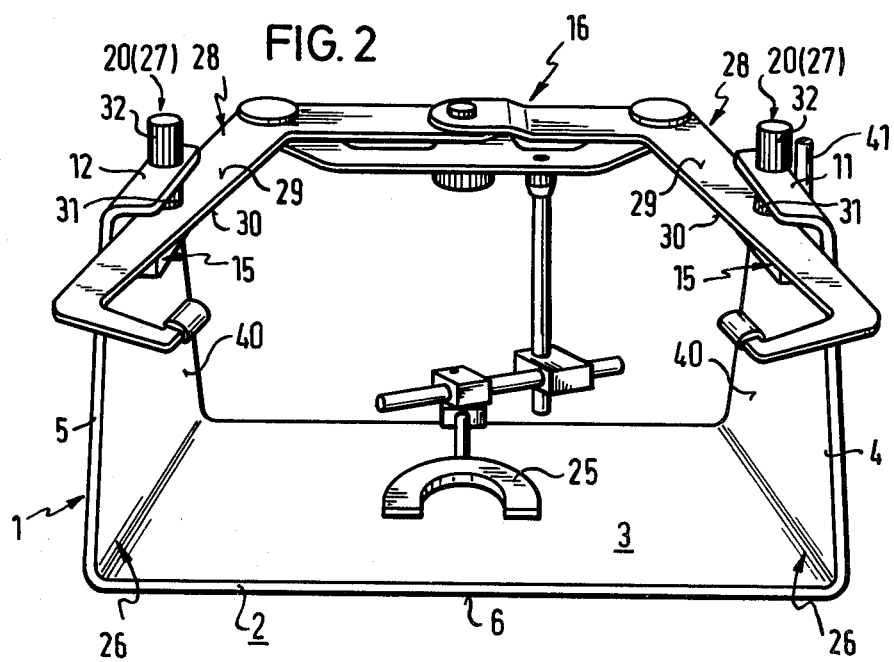
FIG. 2 shows a perspective representation of the combination appliance, with an anatomical transfer bow inserted therein.
Figure 3:
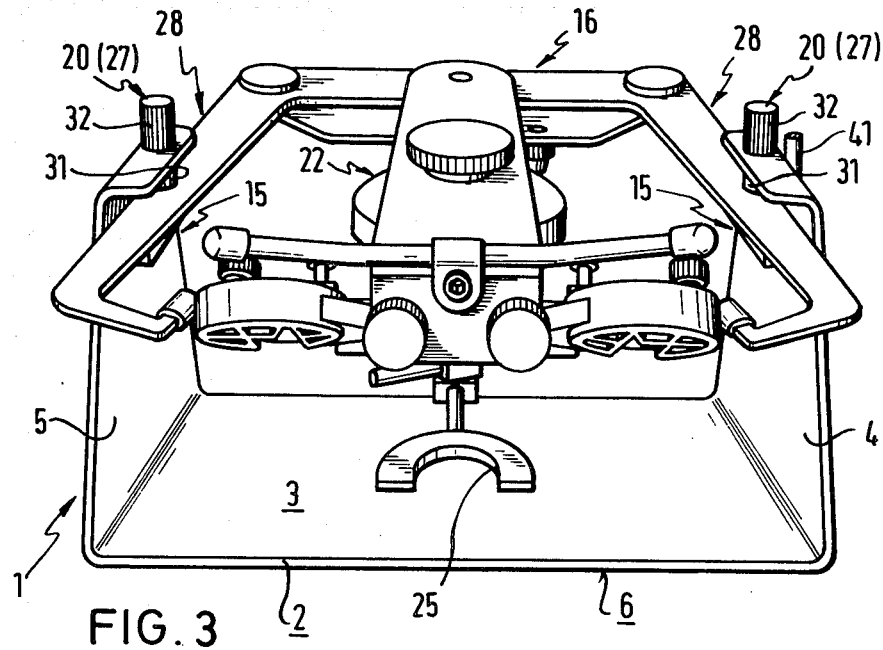
FIG. 3 shows a perspective representation of the combination appliance, with an anatomical transfer bow, together with an upper frame part of a dental articulator, both of which have been inserted into the appliance.

The sidewalls 4 and 5 of the U-shaped cradle are arranged, symmetrically, at an angle with respect to the central axis 8 of the base surface. The angle enclosed by the sidewalls 4, 5 is an acute angle. The free and upward-pointing ends 9 and 10 of the sidewalls 4 and 5 have, in each case, a bent-over portion 11, 12, which is bent over approximately parallel to the base surface 3 and points inwards. The outer edges 13, 14 of the bent-over portions 11, 12 are located opposite each other on the cradle 2. A support 15, for a transfer bow, which is marked 16, in its entirety, in FIGS. 2 and 3, is fitted near the upper end 9, 10 of each sidewall 4, 5. In the embodiment represented, the two supports 15 on the sidewalls 4 and 5 are formed by support rails 17, which are designed as rectangular blocks. The upper surface of each rectangular, block-shaped support rail 17 forms a supporting surface 18 for the transfer bow 16. At the same time, each support rail 17 is arranged at such a distance from the bent-over portion 11, 12 of the upper ends 9, 10 of the sidewalls 4, 5, to which it is assigned in each case, that the transfer bow 16 can be inserted without any obstruction. In order to lock the transfer bow 16, following its insertion into the combination appliance 1, into the interspace formed between the bent-over portions 11 and 12 of the sidewalls 4 and 5 and the supports 15, which are located beneath, an adjustable locking screw 27 is provided in each case. This locking screw 17 permits the transfer bow 16 to be fixed onto the support 15.

Figure 1:
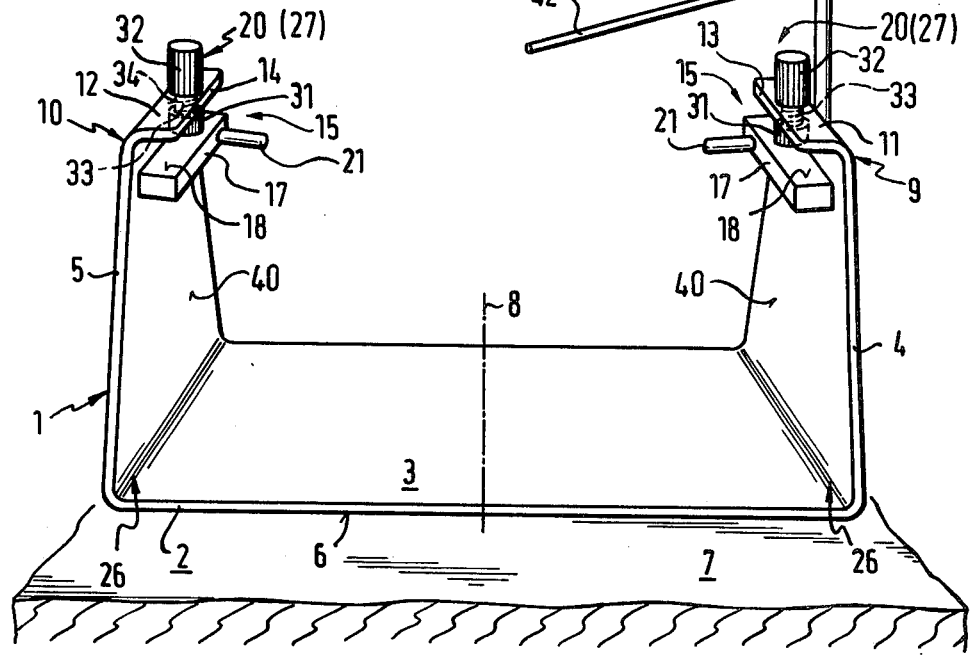
FIG. 1 shows a perspective representation of the combination appliance.

As represented in FIG. 1, a movable pintle, marked 21, is located on each sidewall 4, 5, in the respective support rail 17 for the transfer bow 16, these pintles being intended, as can be seen from FIG. 4, to serve as holding devices for an upper frame part 22 of a dental articulator, and/or for the dental articulator which is marked 23 in its entirety. FIGS. 1 and 4 additionally illustrate the support column 41, with the carrier block 43 and the resilient extension arm 42. The support column 41 projects through the vertically drilled hole 44 in the carrier block 43. The resilient extension arm 42 penetrates the carrier block 43, through the angled drilled hole 45, this hole 45 being disposed in such a way that the extension arm 42 forms an acute angle with that plane of the cast of the upper jaw which extends horizontally.

The Figures clearly show how the sidewalls 4, 5, starting from the transition point 26, smoothly taper from the base surface 3 up to the upper ends 9, 10, so that the width dimension of the sidewalls 4, 5 is greater in the region of the transition point 26 than at the upper ends 9, 10, and/or at the bent-over portions 11, 12.

The mode of operation of the combination appliance 1 is explained in conjunction with FIGS. 2, 3 and 4, in which, according to FIG. 2, only the transfer bow 16 is fixed and, according to FIG. 3, the upper frame part 22 of the dental articulator 23 is additionally held by the transfer bow. FIG. 4 shows how the cast of the opposite jaw is mounted in the dental articulator, by means of plaster of Paris.

According to FIGS. 2 and 3, the transfer bow 16 is inserted, with its side arms 28, either on its own or together with the upper frame part of the dental articulator, in such a way that a bite fork, marked 25 on the diagram, is pointing downwards, that is to say, towards the base surface 3 of the combination appliance. At the same time, the side surfaces 30 of the side arms 28 rest, initially loosely, in the supporting surfaces 18, formed by the support rails 17, for as long as the locking device 20, namely the locking screw 27, is unscrewed.

In FIG. 4, the combination appliance serves to hold the dental articulator, which is marked 23, in its entirety, and to fix the jaw casts against each other.

There follows a brief description, set out in the form of key points, of the working procedure which is adopted with the combination appliance according to the invention.

1. First of all, the upper part of the dental articulator is prepared, by pushing the cutting pin fully upwards, aligning the reference pointer in the fully forward position, setting the inclination of the horizontal condylar joint surface, on both sides, to 30 degrees, and screwing on the mounting plate.
2. The upper part of the articulator is suspended, by means of the pins, which are located on the joint heads of the articulator, in the holes drilled in the end pieces of the anatomical transfer bow, and the unit comprising the upper part of the articulator and the transfer bow is then placed on the support rails 17 of the combination appliance, and fixed, as can be seen from FIG. 3.
3. The bite fork is supported in order to prevent it from dropping down in any way.
4. The upper part of the articulator is swung open and the cast of the upper jaw is placed on the bite fork.
5. The clearance between the secondary base of the cast and the mounting plate is checked by experimentally closing the articulator.
6. The cast is attached to the mounting plate, using quick-setting plaster of Paris with a consistency resembling that of thin cream.
7. After inserting the mounting plate in the lower part of the articulator, the cutting pin is set to the thickness of the centering register, corresponding to a positive value.
8. The pressure-pins of the centering/locking device are fixed in the open position, the straight Benett elements are set to 5 degrees, and the inclination of the horizontal condylar joint surfaces is set to 50 degrees.
9. The upper part of the articulator is suspended on the pintle 21 of the combination appliance, this pintle being located in the longitudinal axis, and is pivoted so that the cast of the upper jaw faces upwards in order to receive the centering register.
10. The cast of the lower jaw is placed on the centering register. If necessary, the inclination can be altered, by adjusting the cutting pin, in order to exclude any possibility of the cast of the lower jaw tilting.
11. A trial closure is made, using the lower part of the articulator. Care must be taken to ensure that sufficient space remains between the mounting plate and the cast of the lower jaw.
12. The cast is attached to the mounting plate, using plaster of Paris with a consistency resembling that of thin cream. The mounting is then checked, using the checking base.

The invention is not, of course, restricted to the configuration and embodiment described and represented, since further configurations of the combination appliance according to the invention can be conceived by a person skilled in the art, and are possible within the scope of the disclosure and the claims.

I claim:

1. Combination appliance for holding and fixing a transfer bow, for pivotably holding and setting the desired angle of inclination of a frame part of an articulator, and for fixing superimposed jaw casts while mounting the cast of the opposite jaw in the articulator, by means of plaster of Paris, said appliance comprising:
    (a) a cradle, of U-shaped cross-section, the sidewalls of said cradle being arranged perpendicularly to the base surface and being arranged so that they converge towards one another, with, on the one hand, the angle of approach corresponding to the angle between the outer edges of the side arms of a transfer bow attached to the upper frame part of the dental articulator, and, on the other hand, the distance between the sidewalls, on the converging side, being small enough to allow articulator frame parts to be hung therein, (b) supports located near the upper ends of the vertical sidewalls of said cradle, and locking devices, located on portions of the upper ends of the vertical sidewalls, for holding and fixing the transfer bow and for pivotably holding and setting the desired angle of inclination of a frame part of an articulator, two pintles located on the inner sides of the vertical sidewalls near those points of the upper ends of the vertical sidewalls which are closest to each other as a result of the approach angle, said pintles being located at right angles to the sidewalls and at least one of the pintles being capable of longitudinal axial movement, and both of said pintels being adapted to project into recesses located in the frame part of the articulator, and (c) a support column, including a carrier block which is adjustable in position along said column and which carries a resilient extension arm, for fixing superimposed jaw casts while the cast of the opposite jaw is being mounted in the articulator by means of plaster of Paris.

2. An appliance as claimed in claim 1, wherein the sidewalls of the U-shaped cradle are arranged, symmetrically, at an angle with respect to the longitudinal axis of the base surface, in such a way that they formed an acute angle, corresponding approximately to the angle enclosed between the outer edges of the side arms of the transfer bow.

3. A receiving cradle as claimed in claim 1 or 2, wherein each support is formed by a rectangular, block-like support rail fastened to the upper end of a respective one of said sidewalls.

4. A receiving cradle as claimed in claim 1 wherein the upper end of each sidewall has a portion which is bent over and points inwards, in a plane approximately parallel to the base surface of the cradle this portion being located sufficiently far from the supporting surface formed by the support which is fitted to the inner side of the sidewall to allow the transfer bow to be inserted without obstruction.

5. A combination appliance as claimed in claim 1 wherein the movable pintle is pressed against the receiving point on the frame part of the articulator.

6. A combination appliance as claimed in claim 1, wherein the pintles possess recesses for receiving projections on the frame parts of the articulator.

7. A combination appliance as claimed in claim 1, wherein the resilient extension arm is a thin resilient plastic rod.

8. A combination appliance as claimed in claim 1 wherein said support column is mounted on one of said sidewalls.

9. A combination appliance as claimed in claim 1 wherein said support column is mounted on a portion of one of said supports.

* * * * *